(12) United States Patent
Wade (10) Patent No.: US 11,978,031 B2
(45) Date of Patent: May 7, 2024

(54) SYSTEMS AND METHODS THAT CREATE A PSEUDO PRESCRIPTION FROM TRANSACTION DATA GENERATED DURING A POINT OF SALE PURCHASE AT A FRONT OF A STORE

(75) Inventor: Devin Wade, Redwood City, CA (US)

(73) Assignee: E2INTERACTIVE, INC., Atlanta, GA (US)

( * ) Notice: Subject to any disclaimer, the term of this patent is extended or adjusted under 35 U.S.C. 154(b) by 0 days.

(21) Appl. No.: 13/118,172

(22) Filed: May 27, 2011

(65) Prior Publication Data

US 2012/0150554 A1 Jun. 14, 2012

Related U.S. Application Data

(60) Provisional application No. 61/422,761, filed on Dec. 14, 2010.

(51) Int. Cl.
| | |
|---|---|
| *G06Q 20/20* | (2012.01) |
| *G06Q 20/38* | (2012.01) |
| *G06Q 30/0207* | (2023.01) |
| *G16H 20/00* | (2018.01) |

(52) U.S. Cl.
CPC ......... *G06Q 20/202* (2013.01); *G06Q 20/387* (2013.01); *G06Q 30/0207* (2013.01); *G16H 20/00* (2018.01)

(58) Field of Classification Search
CPC ...... G06Q 50/22; G06Q 50/24; G06Q 20/202; G06Q 20/387; G06Q 30/0207; G16H 20/00
USPC ........................................................ 705/2–3
See application file for complete search history.

(56) References Cited

U.S. PATENT DOCUMENTS

| | | | |
|---|---|---|---|
| 3,288,350 | A | 11/1966 | Kushner |
| 4,482,802 | A | 11/1984 | Aizawa et al. |
| 4,734,858 | A | 3/1988 | Schlafly |
| 4,747,049 | A | 5/1988 | Richardson et al. |
| 4,877,947 | A | 10/1989 | Mori |
| 4,900,904 | A | 2/1990 | Wright et al. |
| 4,908,521 | A | 3/1990 | Boggan et al. |

(Continued)

FOREIGN PATENT DOCUMENTS

| | | |
|---|---|---|
| CN | 102609839 A | 7/2012 |
| EP | 2128809 A1 | 12/2009 |

(Continued)

OTHER PUBLICATIONS

Patent Cooperation Treaty International Search Report, PCT/US11/43516.

(Continued)

*Primary Examiner* — Eliza A Lam
(74) *Attorney, Agent, or Firm* — LANDMARK INTELLECTUAL PROPERTY LAW, LLC; Gregory M Murphy (57) ABSTRACT

A method is provided for creating a Pseudo-prescription for over the counter items. A retailer infrastructure is provided that includes a point of sale server coupled to a store concentrator and to a product tables/price book(s). An adjudication processor and a claims processor with a process control server are also provided. A Pseudo-prescription is created that contains an NDC for each over-the-counter item being purchased prior to determining if the claims processor.

4 Claims, 7 Drawing Sheets

(56) References Cited

U.S. PATENT DOCUMENTS

| | | |
|---|---|---|
| 4,943,707 A | 7/1990 | Boggan |
| 5,091,634 A | 2/1992 | Finch et al. |
| 5,117,355 A | 5/1992 | McCarthy |
| 5,128,520 A | 6/1992 | Rando |
| 5,202,826 A | 4/1993 | McCarthy |
| 5,231,569 A | 7/1993 | Myatt |
| 5,239,165 A | 8/1993 | Novak |
| 5,255,182 A | 10/1993 | Adams |
| 5,256,863 A | 10/1993 | Ferguson |
| 5,350,906 A | 9/1994 | Brody et al. |
| 5,375,240 A | 12/1994 | Grundy |
| 5,383,113 A | 1/1995 | Kight et al. |
| 5,384,449 A | 1/1995 | Peirce |
| 5,416,306 A | 5/1995 | Imhata |
| 5,500,513 A | 3/1996 | Langhans et al. |
| 5,524,073 A | 6/1996 | Stambler |
| 5,577,109 A | 11/1996 | Stimson et al. |
| 5,590,038 A | 12/1996 | Pitroda |
| 5,602,377 A | 2/1997 | Beller et al. |
| 5,619,569 A | 4/1997 | Kennedy |
| 5,621,201 A | 4/1997 | Langhans et al. |
| 5,657,389 A | 8/1997 | Houvener |
| 5,671,279 A | 9/1997 | Elgamal |
| 5,679,940 A | 10/1997 | Templeton et al. |
| 5,708,780 A | 1/1998 | Levergood |
| 5,729,693 A | 3/1998 | Holda-Fleck |
| 5,740,915 A | 4/1998 | Williams |
| 5,764,981 A | 5/1998 | Veeneman |
| 5,766,143 A | 6/1998 | Sheldon |
| 5,804,803 A | 9/1998 | Cragun |
| 5,806,045 A | 9/1998 | Biorge et al. |
| 5,844,972 A | 12/1998 | Jagadish et al. |
| 5,850,217 A | 12/1998 | Cole |
| 5,857,175 A | 1/1999 | Day |
| 5,889,863 A | 3/1999 | Weber |
| 5,897,625 A | 4/1999 | Gustin |
| 5,903,633 A | 5/1999 | Lorsch |
| 5,903,830 A | 5/1999 | Joao et al. |
| 5,907,142 A | 5/1999 | Kelsey |
| 5,909,492 A | 6/1999 | Payne et al. |
| 5,937,393 A | 8/1999 | O'Leary et al. |
| 5,945,653 A | 8/1999 | Walker et al. |
| 5,950,173 A | 9/1999 | Perkowski |
| 5,956,695 A | 9/1999 | Carrithers et al. |
| 5,968,110 A | 10/1999 | Westrope |
| 5,991,750 A | 11/1999 | Watson |
| 5,999,624 A | 12/1999 | Hopkins |
| 6,000,608 A | 12/1999 | Dorf |
| 6,003,014 A | 12/1999 | Lee et al. |
| 6,012,049 A | 1/2000 | Kawan |
| 6,014,635 A | 1/2000 | Harris |
| 6,018,719 A | 1/2000 | Rogers |
| 6,021,397 A | 2/2000 | Jones et al. |
| 6,029,139 A | 2/2000 | Bezos |
| 6,032,133 A | 2/2000 | Hilt et al. |
| 6,032,135 A | 2/2000 | Molano et al. |
| 6,032,859 A | 3/2000 | Muehlberger et al. |
| 6,039,244 A | 3/2000 | Finsterwald |
| 6,047,270 A | 4/2000 | Joao et al. |
| 6,058,300 A | 5/2000 | Hanson |
| 6,058,382 A | 5/2000 | Kasai et al. |
| 6,070,147 A | 5/2000 | Harms et al. |
| 6,072,870 A | 6/2000 | Nguyen et al. |
| 6,085,242 A | 7/2000 | Chandra |
| 6,086,187 A | 7/2000 | Iguchi |
| 6,092,053 A | 7/2000 | Boesch et al. |
| 6,098,053 A | 8/2000 | Slater |
| 6,108,642 A | 8/2000 | Findley |
| 6,119,099 A | 9/2000 | Walker |
| 6,119,105 A | 9/2000 | Williams |
| 6,125,352 A | 9/2000 | Franklin |
| 6,134,533 A | 10/2000 | Shell |
| 6,138,911 A | 10/2000 | Fredregil |
| 6,154,738 A | 11/2000 | Call |
| 6,158,657 A | 12/2000 | Hall, III et al. |
| 6,173,272 B1 | 1/2001 | Thomas et al. |
| 6,182,894 B1 | 2/2001 | Hackett et al. |
| 6,189,787 B1 | 2/2001 | Dorf |
| 6,222,914 B1 | 4/2001 | McMullin |
| 6,226,624 B1 | 5/2001 | Watson et al. |
| 6,267,670 B1 | 7/2001 | Walker |
| 6,302,326 B1 | 10/2001 | Symonds et al. |
| 6,304,860 B1 | 10/2001 | Martin |
| 6,304,915 B1 | 10/2001 | Nguyen et al. |
| 6,315,193 B1 | 11/2001 | Hogan |
| 6,317,028 B1 | 11/2001 | Valiulis |
| 6,334,116 B1 | 12/2001 | Ganesan et al. |
| 6,360,254 B1 | 3/2002 | Linden |
| 6,418,414 B1 | 7/2002 | Lutz et al. |
| 6,418,441 B1 | 7/2002 | Call |
| 6,422,462 B1 | 7/2002 | Cohen |
| 6,424,706 B1 | 7/2002 | Katz et al. |
| 6,442,532 B1 | 8/2002 | Kawan |
| 6,473,500 B1 | 10/2002 | Risafi et al. |
| 6,473,739 B1 | 10/2002 | Showghi et al. |
| 6,494,367 B1 | 12/2002 | Zacharias |
| 6,502,745 B1 | 1/2003 | Stimson et al. |
| 6,507,823 B1 | 1/2003 | Nel |
| 6,529,880 B1 | 3/2003 | McKeen et al. |
| 6,529,956 B1 | 3/2003 | Smith |
| 6,536,659 B1 | 3/2003 | Hauser |
| 6,575,361 B1 | 6/2003 | Graves et al. |
| 6,594,644 B1 | 7/2003 | Van Dusen |
| 6,609,106 B1 | 8/2003 | Robertson |
| 6,636,833 B1 | 10/2003 | Flitcroft |
| 6,648,222 B2 | 11/2003 | McDonald et al. |
| 6,675,153 B1 | 1/2004 | Cook et al. |
| 6,678,664 B1 | 1/2004 | Ganesan |
| 6,736,314 B2 | 5/2004 | Cooper et al. |
| 6,827,260 B2 | 12/2004 | Stoutenburg et al. |
| 6,829,596 B1 | 12/2004 | Frazee |
| 6,836,765 B1 | 12/2004 | Sussman |
| 6,862,575 B1 | 3/2005 | Anttila |
| 6,886,742 B2 | 5/2005 | Stoutenburg et al. |
| 6,899,621 B2 | 5/2005 | Behm |
| 6,915,277 B1 | 7/2005 | Manchester |
| 6,918,537 B2 | 7/2005 | Graves et al. |
| 6,932,268 B1 | 8/2005 | McCoy et al. |
| 6,948,063 B1 | 9/2005 | Ganesan et al. |
| 6,965,866 B2 | 11/2005 | Klein |
| 6,993,610 B2 | 1/2006 | Guy |
| 7,055,740 B1 | 6/2006 | Schultz |
| 7,072,864 B2 | 7/2006 | Brake, Jr. et al. |
| 7,083,084 B2 | 8/2006 | Graves et al. |
| 7,086,586 B1 | 8/2006 | Sullivan |
| 7,093,761 B2 | 8/2006 | Smith et al. |
| 7,103,577 B2 | 9/2006 | Blair et al. |
| 7,108,183 B1 | 9/2006 | Cox, Jr. |
| 7,111,780 B2 | 9/2006 | Broussard et al. |
| 7,209,889 B1 | 4/2007 | Whitfield |
| 7,216,092 B1 | 5/2007 | Weber |
| 7,252,226 B2 | 8/2007 | Risafi et al. |
| 7,281,653 B2 | 10/2007 | Beck et al. |
| 7,292,998 B2 | 11/2007 | Graves et al. |
| 7,316,350 B2 | 1/2008 | Algiene |
| 7,328,190 B2 | 2/2008 | Smith et al. |
| 7,343,406 B1 | 3/2008 | Buonanno |
| 7,363,265 B2 | 4/2008 | Horgan |
| 7,434,729 B2 | 10/2008 | Cracchiolo |
| 7,437,328 B2 | 10/2008 | Graves et al. |
| 7,494,417 B2 | 2/2009 | Walker |
| 7,513,422 B1 | 4/2009 | Tucker |
| 7,566,000 B2 | 7/2009 | Agostino et al. |
| 7,590,557 B2 | 9/2009 | Harrison |
| 7,631,803 B2 | 12/2009 | Peyret |
| 7,650,308 B2 | 1/2010 | Nguyen et al. |
| 7,653,599 B2 | 1/2010 | Doran et al. |
| 7,702,542 B2 | 4/2010 | Aslanian |
| 7,711,598 B2 | 5/2010 | Perkowski |
| 7,747,644 B1 | 6/2010 | Reihl |
| 7,757,944 B2 | 7/2010 | Cline et al. |
| 7,767,944 B2 | 7/2010 | Cline |
| 7,789,695 B2 | 8/2010 | Robinson |
| 7,848,948 B2 | 12/2010 | Perkowski et al. |

(56) References Cited

U.S. PATENT DOCUMENTS

| | | |
|---|---|---|
| 7,866,548 B2 | 1/2011 | Reed et al. |
| 7,904,333 B1 | 3/2011 | Perkowski |
| 7,905,399 B2 | 3/2011 | Barnes |
| 7,922,083 B2 | 4/2011 | Harrison |
| 7,949,543 B2 | 5/2011 | Chan et al. |
| 7,970,626 B2 | 6/2011 | Cracchiolo |
| 8,036,953 B2 | 10/2011 | Hsu et al. |
| 8,046,268 B2 | 10/2011 | Hunt |
| 8,103,520 B2 | 1/2012 | Mueller |
| 8,152,060 B2 | 4/2012 | Wolfe et al. |
| 8,152,061 B2 | 4/2012 | Wolfe et al. |
| 8,181,867 B1 | 5/2012 | Bierbaum et al. |
| 8,245,910 B2 | 8/2012 | Sullivan et al. |
| 8,265,050 B2 | 9/2012 | Howe |
| 8,265,950 B2 | 9/2012 | Howe et al. |
| 8,267,313 B2 | 9/2012 | Harper et al. |
| 8,332,277 B2 | 12/2012 | Mccaffery et al. |
| 8,332,323 B2 | 12/2012 | Stals |
| 8,352,627 B1 | 1/2013 | Harris |
| 8,396,758 B2 | 3/2013 | Paradise |
| 8,509,814 B1 | 8/2013 | Parker |
| 8,577,735 B2 | 11/2013 | Wilen |
| 8,631,999 B2 | 1/2014 | Wolfe et al. |
| 8,636,203 B1 | 1/2014 | Patterson |
| 8,662,387 B1 | 3/2014 | Geller |
| 8,712,835 B1 | 4/2014 | Philyaw |
| 8,751,298 B1 | 6/2014 | Giordano et al. |
| 8,768,834 B2 | 7/2014 | Zacarias et al. |
| 9,098,190 B2 | 8/2015 | Zhou |
| 9,183,534 B2 | 11/2015 | Gharabally |
| 9,449,343 B2 | 9/2016 | Mayerle |
| 9,483,786 B2 | 11/2016 | Glass |
| 9,626,070 B2 | 4/2017 | Cowles |
| 9,672,687 B2 | 6/2017 | Cage |
| 10,262,346 B2 | 4/2019 | Glass |
| 10,515,397 B2 | 12/2019 | Serfass |
| 10,679,268 B1 | 6/2020 | Kochhar |
| 2001/0034609 A1 | 10/2001 | Dovolis |
| 2001/0037264 A1 | 11/2001 | Husemann et al. |
| 2001/0056410 A1 | 12/2001 | Ishigaki |
| 2002/0002495 A1* | 1/2002 | Ullman ............... G07F 17/0092 705/21 |
| 2002/0010627 A1 | 1/2002 | Lerat |
| 2002/0016749 A1 | 2/2002 | Borecki et al. |
| 2002/0062249 A1 | 5/2002 | Iannacci |
| 2002/0065713 A1 | 5/2002 | Awada et al. |
| 2002/0069139 A1 | 6/2002 | Bernstein et al. |
| 2002/0070270 A1 | 6/2002 | Narita et al. |
| 2002/0088855 A1 | 7/2002 | Hodes |
| 2002/0091573 A1 | 7/2002 | Hodes |
| 2002/0095420 A1 | 7/2002 | Hovsepian |
| 2002/0116531 A1 | 8/2002 | Chu |
| 2002/0128859 A1 | 9/2002 | Perkowski |
| 2002/0130176 A1 | 9/2002 | Suzuki |
| 2002/0138573 A1 | 9/2002 | Saguy |
| 2002/0153410 A1 | 10/2002 | Santini |
| 2002/0198831 A1 | 12/2002 | Patricelli et al. |
| 2003/0004802 A1 | 1/2003 | Callegari |
| 2003/0009382 A1 | 1/2003 | D'Arbeloff |
| 2003/0033246 A1 | 2/2003 | Slater |
| 2003/0055782 A1 | 3/2003 | Slater |
| 2003/0061162 A1 | 3/2003 | Matthews |
| 2003/0069846 A1 | 4/2003 | Marcon |
| 2003/0080186 A1 | 5/2003 | McDonald et al. |
| 2003/0088462 A1 | 5/2003 | Carrithers et al. |
| 2003/0105688 A1 | 6/2003 | Brown et al. |
| 2003/0121967 A1 | 7/2003 | Goldberg et al. |
| 2003/0126079 A1 | 7/2003 | Roberson |
| 2003/0154163 A1 | 8/2003 | Phillips et al. |
| 2003/0163787 A1 | 8/2003 | Hay et al. |
| 2003/0172039 A1 | 9/2003 | Guy |
| 2003/0197059 A1 | 10/2003 | Tidball et al. |
| 2003/0200179 A1 | 10/2003 | Kwan |
| 2003/0204441 A1 | 10/2003 | Ellis et al. |
| 2003/0212796 A1 | 11/2003 | Willard |
| 2003/0234819 A1 | 12/2003 | Daly et al. |
| 2004/0024697 A1 | 2/2004 | Landa et al. |
| 2004/0054587 A1 | 3/2004 | Dev et al. |
| 2004/0065726 A1 | 4/2004 | McGee et al. |
| 2004/0117302 A1 | 6/2004 | Weichert et al. |
| 2004/0138921 A1 | 7/2004 | Broussard et al. |
| 2004/0153344 A1 | 8/2004 | Bui |
| 2004/0182922 A1 | 9/2004 | Talarico, Jr. |
| 2004/0185881 A1 | 9/2004 | Lee |
| 2004/0193464 A1 | 9/2004 | Szrek |
| 2004/0193490 A1 | 9/2004 | Pletz |
| 2004/0206814 A1 | 10/2004 | Kawai et al. |
| 2004/0215573 A1 | 10/2004 | Frederick et al. |
| 2004/0224660 A1 | 11/2004 | Anderson |
| 2004/0225560 A1 | 11/2004 | Lewis et al. |
| 2004/0260647 A1 | 12/2004 | Blinn et al. |
| 2004/0267663 A1 | 12/2004 | Karns |
| 2005/0004837 A1 | 1/2005 | Sweeny |
| 2005/0027624 A1 | 2/2005 | Cai |
| 2005/0045732 A1 | 3/2005 | Whitaker |
| 2005/0051619 A1 | 3/2005 | Graves et al. |
| 2005/0071268 A1 | 3/2005 | Riddett, Jr. |
| 2005/0086168 A1 | 4/2005 | Alvarez |
| 2005/0116028 A1 | 6/2005 | Cotten |
| 2005/0165682 A1 | 7/2005 | Duke |
| 2005/0167481 A1 | 8/2005 | Hansen et al. |
| 2005/0177517 A1 | 8/2005 | Leung |
| 2005/0182695 A1 | 8/2005 | Lubow et al. |
| 2005/0187793 A1 | 8/2005 | Myles |
| 2005/0197919 A1 | 9/2005 | Robertson |
| 2005/0203844 A1 | 9/2005 | Ferguson et al. |
| 2005/0233797 A1 | 10/2005 | Gilmore |
| 2005/0240477 A1 | 10/2005 | Friday |
| 2005/0261968 A1 | 11/2005 | Randall et al. |
| 2005/0274793 A1 | 12/2005 | Cantini |
| 2006/0004631 A1 | 1/2006 | Roberts et al. |
| 2006/0010007 A1 | 1/2006 | Denman |
| 2006/0037835 A1 | 2/2006 | Doran |
| 2006/0041470 A1 | 2/2006 | Filho et al. |
| 2006/0053056 A1 | 3/2006 | Alspach-Goss et al. |
| 2006/0058011 A1 | 3/2006 | Vanska |
| 2006/0069642 A1 | 3/2006 | Doran et al. |
| 2006/0078100 A1 | 4/2006 | Risafi et al. |
| 2006/0080174 A1 | 4/2006 | Veeneman |
| 2006/0089160 A1 | 4/2006 | Othmer |
| 2006/0106642 A1 | 5/2006 | Reicher et al. |
| 2006/0113376 A1 | 6/2006 | Reed et al. |
| 2006/0212346 A1 | 9/2006 | Soza |
| 2006/0224450 A1 | 10/2006 | Moon |
| 2006/0253320 A1 | 11/2006 | Heywood |
| 2006/0255125 A1 | 11/2006 | Jennings |
| 2006/0261150 A1 | 11/2006 | Seifert et al. |
| 2006/0277146 A1 | 12/2006 | Dively et al. |
| 2007/0011025 A1 | 1/2007 | Cracchiolo |
| 2007/0017975 A1 | 1/2007 | Lewis et al. |
| 2007/0021969 A1 | 1/2007 | Homeier-Beals |
| 2007/0030824 A1 | 2/2007 | Ribaudo |
| 2007/0038577 A1 | 2/2007 | Werner |
| 2007/0043682 A1 | 2/2007 | Drapkin et al. |
| 2007/0055785 A1 | 3/2007 | Stevens |
| 2007/0063024 A1 | 3/2007 | Guillot |
| 2007/0156436 A1 | 4/2007 | Fisher |
| 2007/0114274 A1 | 5/2007 | Gibbs |
| 2007/0125838 A1 | 6/2007 | Law et al. |
| 2007/0136149 A1 | 6/2007 | Woodward et al. |
| 2007/0162338 A1 | 7/2007 | Lawe |
| 2007/0174123 A1 | 7/2007 | Dorr |
| 2007/0175985 A1 | 8/2007 | Barnes et al. |
| 2007/0192182 A1 | 8/2007 | Monaco |
| 2007/0198433 A1 | 8/2007 | McGee et al. |
| 2007/0208632 A1 | 9/2007 | Downes et al. |
| 2007/0214005 A1 | 9/2007 | Kennedy |
| 2007/0214080 A1 | 9/2007 | Babi et al. |
| 2007/0251995 A1 | 11/2007 | Kingsborough et al. |
| 2007/0257767 A1 | 11/2007 | Beeson |
| 2007/0265872 A1 | 11/2007 | Robinson et al. |
| 2007/0284434 A1 | 12/2007 | Fletcher |
| 2008/0011820 A1 | 1/2008 | Brown et al. |
| 2008/0028395 A1 | 1/2008 | Motta et al. |

(56) References Cited

U.S. PATENT DOCUMENTS

| | | |
|---|---|---|
| 2008/0033857 A1 | 2/2008 | Moses |
| 2008/0040285 A1 | 2/2008 | Rackley |
| 2008/0052169 A1 | 2/2008 | O'Shea et al. |
| 2008/0059226 A1 | 3/2008 | Melker |
| 2008/0059318 A1 | 3/2008 | Packes et al. |
| 2008/0070690 A1 | 3/2008 | Van Luchene |
| 2008/0078831 A1 | 4/2008 | Johnson et al. |
| 2008/0097851 A1 | 4/2008 | Bemmel et al. |
| 2008/0133266 A1 | 6/2008 | Allen |
| 2008/0133351 A1 | 6/2008 | White et al. |
| 2008/0162341 A1 | 7/2008 | Zimmer et al. |
| 2008/0179395 A1 | 7/2008 | Dixon et al. |
| 2008/0183627 A1 | 7/2008 | Harrison et al. |
| 2008/0209611 A1 | 8/2008 | Silverbrook |
| 2008/0215361 A1 | 9/2008 | Nunnari et al. |
| 2008/0255942 A1 | 10/2008 | Craft |
| 2008/0319868 A1 | 12/2008 | Briscoe |
| 2009/0006116 A1 | 1/2009 | Baker |
| 2009/0037326 A1 | 2/2009 | Chitti et al. |
| 2009/0076896 A1 | 3/2009 | DeWitt |
| 2009/0078755 A1 | 3/2009 | Sullivan et al. |
| 2009/0094126 A1 | 4/2009 | Killian et al. |
| 2009/0111378 A1 | 4/2009 | Sheynman |
| 2009/0112709 A1 | 4/2009 | Barhydt et al. |
| 2009/0144161 A1 | 6/2009 | Fisher |
| 2009/0157487 A1 | 6/2009 | Cottrell et al. |
| 2009/0157554 A1 | 6/2009 | Hobson et al. |
| 2009/0163263 A1 | 6/2009 | Herndon |
| 2009/0164329 A1* | 6/2009 | Bishop ............... G06Q 20/02 705/19 |
| 2009/0171739 A1 | 7/2009 | De et al. |
| 2009/0172561 A1 | 7/2009 | Kane |
| 2009/0173782 A1 | 7/2009 | Muscato |
| 2009/0173784 A1 | 7/2009 | Yang |
| 2009/0187491 A1 | 7/2009 | Bull |
| 2009/0192904 A1* | 7/2009 | Patterson ............ G06Q 20/20 705/17 |
| 2009/0192928 A1 | 7/2009 | Abifaker |
| 2009/0197684 A1 | 8/2009 | Arezina |
| 2009/0240516 A1 | 9/2009 | Palestrant |
| 2009/0240579 A1 | 9/2009 | Skowreonek |
| 2009/0247131 A1 | 10/2009 | Champion |
| 2009/0254432 A1 | 10/2009 | Mccaffery et al. |
| 2009/0259589 A1 | 10/2009 | Agostino et al. |
| 2009/0281941 A1 | 11/2009 | Worth |
| 2009/0287558 A1 | 11/2009 | Seth et al. |
| 2009/0298427 A1 | 12/2009 | Wilkinson |
| 2009/0319352 A1 | 12/2009 | Boyle et al. |
| 2010/0005424 A1 | 1/2010 | Sundaresan |
| 2010/0008535 A1 | 1/2010 | Abulafia |
| 2010/0010906 A1 | 1/2010 | Grecia |
| 2010/0010909 A1 | 1/2010 | Marshall et al. |
| 2010/0041368 A1 | 2/2010 | Kumar |
| 2010/0042471 A1 | 2/2010 | Chang |
| 2010/0057580 A1 | 3/2010 | Raghunathan |
| 2010/0082490 A1 | 4/2010 | Rosenblatt |
| 2010/0088188 A1 | 4/2010 | Kumar et al. |
| 2010/0097180 A1 | 4/2010 | Cardullo |
| 2010/0131415 A1 | 5/2010 | Sartipi |
| 2010/0185461 A1 | 7/2010 | Broeska et al. |
| 2010/0185505 A1 | 7/2010 | Sprogoe |
| 2010/0205063 A1 | 8/2010 | Mersky |
| 2010/0235290 A1 | 9/2010 | Junger |
| 2010/0293536 A1 | 11/2010 | Nikitin |
| 2010/0299194 A1 | 11/2010 | Snyder et al. |
| 2010/0304852 A1 | 12/2010 | Szrek |
| 2010/0312636 A1 | 12/2010 | Coulter et al. |
| 2011/0035268 A1 | 2/2011 | Rossi |
| 2011/0040684 A1 | 2/2011 | Beck et al. |
| 2011/0057027 A1 | 3/2011 | Grossman |
| 2011/0060904 A9 | 3/2011 | Whitfield |
| 2011/0087592 A1 | 4/2011 | Van Der et al. |
| 2011/0091092 A1 | 4/2011 | Nepomniachtchi |
| 2011/0106698 A1 | 5/2011 | Isaacson |
| 2011/0161226 A1 | 6/2011 | Courtion |
| 2011/0166872 A1 | 7/2011 | Cervenka et al. |
| 2011/0166992 A1 | 7/2011 | Dessert et al. |
| 2011/0173083 A1 | 7/2011 | Reed et al. |
| 2011/0202419 A1 | 8/2011 | Mamdani |
| 2011/0234514 A1 | 9/2011 | Gothard |
| 2011/0246284 A1 | 10/2011 | Chaikin |
| 2012/0060425 A1 | 3/2012 | Yamauchi et al. |
| 2012/0089467 A1 | 4/2012 | Comparelli |
| 2012/0099780 A1 | 4/2012 | Smith |
| 2012/0136780 A1 | 5/2012 | El-Awady |
| 2012/0203572 A1 | 8/2012 | Christense |
| 2012/0209688 A1 | 8/2012 | Lamothe et al. |
| 2012/0234911 A1 | 9/2012 | Yankovich |
| 2012/0245987 A1 | 9/2012 | Isaacson |
| 2012/0271689 A1 | 10/2012 | Etheredge |
| 2012/0284185 A1 | 11/2012 | Mettler |
| 2012/0290366 A1 | 11/2012 | Giles |
| 2012/0303425 A1 | 11/2012 | Katzin |
| 2013/0073388 A1 | 3/2013 | Heath |
| 2013/0179177 A1 | 7/2013 | Dhavle et al. |
| 2013/0226728 A1 | 8/2013 | Oghittu |
| 2013/0290121 A1 | 10/2013 | Simakov |
| 2013/0304561 A1 | 11/2013 | Warner et al. |
| 2014/0006268 A1 | 1/2014 | Roberts |
| 2014/0019238 A1 | 1/2014 | Blatchley |
| 2014/0058873 A1 | 2/2014 | Sorenson |
| 2014/0074704 A1 | 3/2014 | White |
| 2014/0297437 A1 | 3/2014 | Natarajan |
| 2014/0164159 A1 | 6/2014 | Lovelace |
| 2014/0081769 A1 | 11/2014 | Wilen |
| 2014/0279187 A1 | 11/2014 | Gopinath |
| 2015/0066757 A1 | 3/2015 | Shenoy |
| 2015/0178701 A1 | 6/2015 | Glass |
| 2015/0278845 A1 | 10/2015 | Sorem et al. |
| 2017/0076293 A1 | 3/2017 | Cage |

FOREIGN PATENT DOCUMENTS

| | | |
|---|---|---|
| JP | 2002189963 A | 7/2002 |
| JP | 2003208541 A | 7/2003 |
| JP | 2008541303 A | 11/2008 |
| JP | 2010521017 A | 6/2010 |
| KR | 20020027427 A | 4/2002 |
| WO | 2013078499 A1 | 6/2013 |

OTHER PUBLICATIONS

Patent Cooperation Treaty International Search Report, PCT/US11/64388.

Patent Cooperation Treaty International Search Report, PCT/US 11/64384.

Patent Cooperation Treaty International Search Report, PCT/US2011/064411.

Patent Cooperation Treaty International Search Report, PCT/US2011/064405.

SIGIS: Special Interest Group for IIAS Standards. SIGIS Eligible Product List Criteria for Supporting Private Label Items. 2007. [retrieved on Mar. 28, 2012]. Retrieved from the Internet: http://portal.sig-is.org/en/join/documents/SIGISPrivateLabelEligibilityCriteriaPolicy-12-12-07-1.pdf>entire document.

ADP National Account Services. Important information for FSA Plans and Health Care Reform.

* cited by examiner

FIG. 5 and more particularly to systems and methods that process that create the Pseudo-prescription from transaction data generated during a point-of-sale purchase at the front of the store.

SYSTEMS AND METHODS THAT CREATE A PSEUDO PRESCRIPTION FROM TRANSACTION DATA GENERATED DURING A POINT OF SALE PURCHASE AT A FRONT OF A STORE

RELATED APPLICATIONS

This application claims the benefit of U.S. Ser. No. 61/422,761, filed Dec. 14, 2010, U.S. Ser. No. 13/117,003, filed May 26, 2011, and U.S. Ser. No. 13/117,010, filed May 26, 2011, all of which are incorporated by reference.

FIELD OF THE INVENTION

The present invention relates generally to systems and methods for facilitating a process for creating a Pseudo-prescription for over the counter items, paid for by paid for by health care payers, using data generated from a point-of-sale transaction at retailers, and more particularly to systems and methods that process that create the Pseudo-prescription from transaction data generated during a point-of-sale purchase at the front of the store.

DESCRIPTION OF THE RELATED ART

Over-the-counter medicated items are utilized by nearly 90% of the U.S. population to treat minor health ailments. Americans use over-the-counter items to self-medicate a health episode that was self-diagnosed. Over-the-counter items do not require a prescription and are available at nearly 750,000 retail locations in the U.S. as compared with only 75,000 pharmacy locations that dispense prescribed items. It has been proven that the use of over-the-counter items saves the U.S. healthcare system billions of dollars each year by way of reduced doctor and emergency room visits as a result of early detection, self-diagnosis and self-medication.

Many health plans, including the federal government through the Department of Health and Human Services and more specifically, the centers for Medicare and Medicaid, provide benefit coverage for the use of over-the-counter medications. For prescribed items, payers such as federal and state governments through Medicare and Medicaid contract with entities, typically pharmacy benefits managers, who approve and settle payment with the dispensers of the prescribed item.

This process allows customers to purchase prescribed items without paying for them at the point of purchase because the dispenser is able to connect in real-time and submit the prescription required for the item to the pharmacy benefits manager. The pharmacy benefits manager approves the prescription and settles payment with the dispenser and then receives the funds from the payer. In this example the federal or state agencies contract with them to perform such services.

There have been several attempts to include non-prescribed items in the process described above for prescribed items. All require a prescription because the entire system for processing prescription is based on that foundation. None have been successful and are likely to reduce the use of items that do not require a prescription, over-the-counter items, costing the healthcare system billions of dollars.

There is a need for systems and methods that provide customers the ability to purchase over-the-counter items from the front of a store without a prescription using the normal process for purchasing over-the-counter items.

There is a need for systems and methods that that create a Pseudo-prescription for over the counter items from transaction data generated during a point-of-sale purchase at a front of the store. The Pseudo-prescription can then be submitted to the pharmacy benefits manager during the purchase and the existing process in place of approving the Pseudo-prescription and the subsequent funds flow leveraged.

SUMMARY

Accordingly, an object of the present invention is to provide systems and methods that create a Pseudo-prescription for over the counter items from transaction data generated during a point-of-sale purchase at the front of a store.

Another object of the present invention is to provide systems and methods that allow front of store transactions at participating retailers that sell over-the-counter items to create proxies (Pseudo-prescription) for over-the-counter items from transaction data.

Yet another object of the present invention is to provide systems and methods that allow front of store transactions to sell over-the-counter items to create proxies (Pseudo-prescription) from transaction data, eliminating the need for a customer to visit a doctor to request a prescription for an item that does not require a prescription because the prescription is the only way to associate the purchase with the customers benefits coverage.

These and other objects of the present invention are achieved in, a method for creating a Pseudo-prescription for over the counter items. A retailer infrastructure is provided that includes a point of sale server coupled to a store concentrator and to a product tables/price book(s). An adjudication processor and a claims processor with a process control server are also provided. A Pseudo-prescription is created that contains an NDC for each over-the-counter item being purchased prior to determining if the claims processor.

DETAILED DESCRIPTION

Systems and methods are provided for facilitating multiple retailers to automate the process of matching items presented at point of purchase with the buyer selected financial transaction financial transaction card to determine if the items presented are permitted to be purchased by the presented financial transaction financial transaction card. More particularly, the present invention provides for the matching of items to multiple item lists for sponsor associated payment/settlement programs.

With the present invention, systems and methods are provided for implementing a financial transaction card program having buyers. The buyers are restricted to purchase select items from select retailers and the retailers are part of a private host-to-host network having the ability to communicate messages to and from a network computer. Each buyer has a unique identification code that corresponds with a list of selected items and a list of selected retailers.

With the present invention, systems and methods are provided to implement an adjudication process which allows a market basket utilized with product catalogs. Each catalog contains a list of Universal Product Codes ("UPC"), each identifying an item that can be purchased by a financial transaction card. A purse is an identifier for a financial account associated with a financial transaction card. As non-limiting examples, the financial account can be a bank account, credit financial transaction card, debit financial transaction card, pre-paid financial transaction card, a third party funding source and the like. As non-limiting examples, a financial transaction card can be, the financial transaction card is selected from at least one of, credit financial transaction card, debit financial transaction card, gift financial transaction card, fund transfer financial transaction card, other types of payment authenticating piece capable of carrying out a transfer of funds and the like In one embodiment, a financial transaction card, including but not limited to a debit or credit financial transaction card, has multiple financial transaction institutions or purses. The financial transaction card can also have only one spending purse. Items in the market basket are adjudicated against the one or more associated catalogs.

Figure 1:
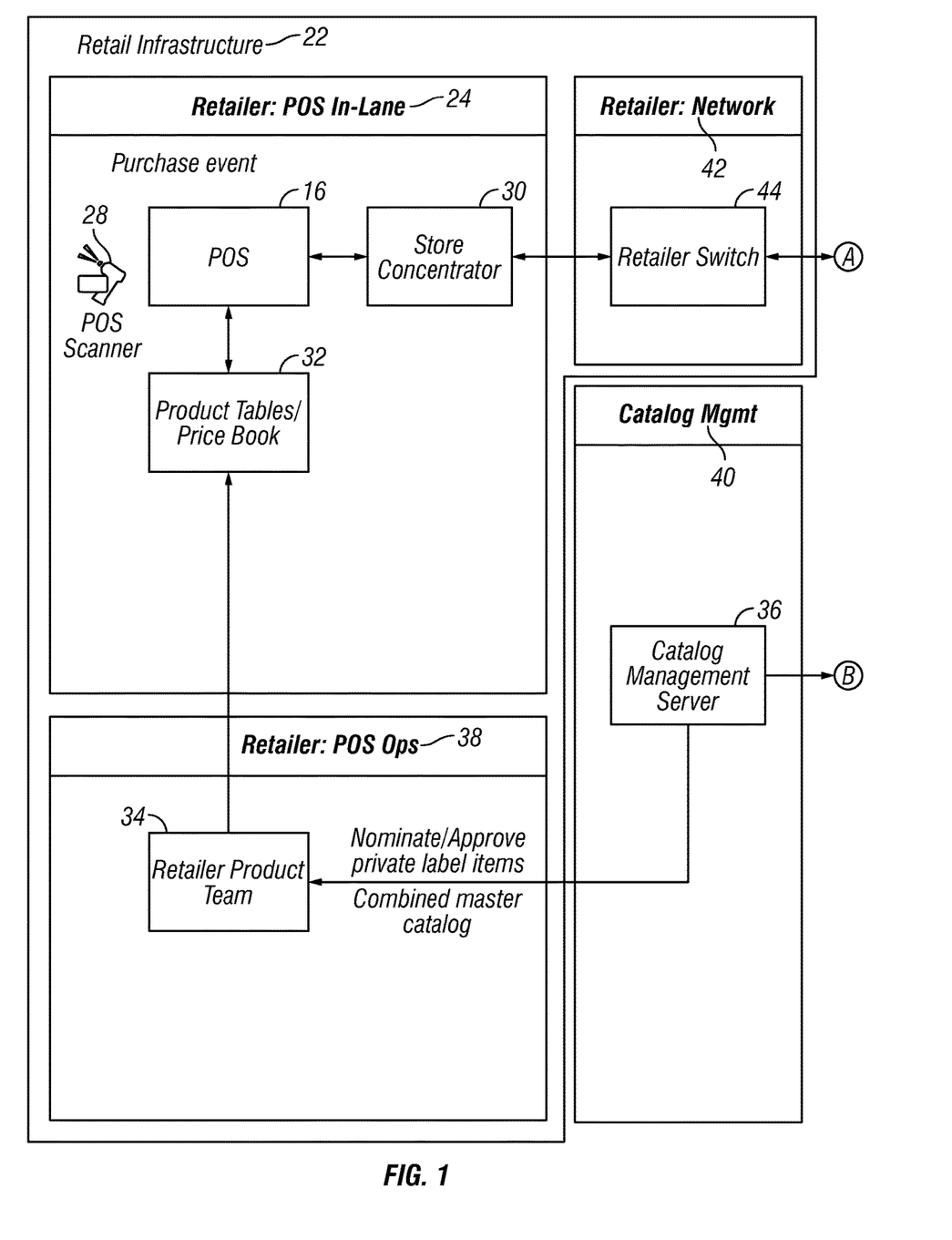
FIG. 1 is an overall system architecture of one embodiment of the present invention outside of a retailer network infrastructure.

As illustrated in FIG. 1, an adjudication processor 10 includes a market basket analysis server 12, a process control server 14, a switch 16, product catalogs 18 and buyer account data 20.

More generally, in FIG. 1, a retailer infrastructure, denoted as 22, includes a retailer:POS In-Lane 24, hereafter (retailer 24). The retailer 24 includes a point of sale server (POS) 26, with a bar code scanner 28, that is coupled to a store concentrator 30 and to a product tables/price book(s) 32. A retailer product team 34 is in communication with the product tables/price book(s) 32 and to a catalog management server 36. The retailer product team 34 is part of a retailer: POS Ops 38.

The catalog management server 36 is included in a catalog management processor 40. The retailer infrastructure 22 also includes a retailer network 42 with a retailer switch 44.

The retailer switch 44 is coupled to the adjudication processor 10. The market basket analysis server 12 is coupled to the product catalogs 18 and validates eligible items in the market basket, as more fully discussed hereafter. The contents of the market basket, including but not limited to, UPC, price, quantity and the like, are communicated between the market basket analysis server 12 and the switch 16, from the retailer switch 44. The catalog management server 36 communicates with the market basket analysis server 12 in the form of the product catalogs 18.

A financial transaction card issuer, hereafter (financial processor 46) is coupled to the adjudication processor 10 and includes financial transaction card numbers 48 and an issuer processor (transactions) 50.

A benefits processor 52 includes a claims processor (accumulator) 54 coupled to switch 16. The benefits processor 52 is in communication with the switch 16. The market basket analysis server 12 can contact the benefit processor 52 via the switch 16 in real time and receive a claim authorization. The benefits processor 52 can communicate via standard prescription languages, NCPDP5.1 and NCPDP d.0.

Account information 56 includes buyer account data 20 that is provided to the market basket analysis server 12 and relates to financial transaction financial transaction card numbers 48, originating with the financial processor 46 that includes an issuer processor 50 (transactions). The issuer processor 50 communicates with a switch 58 and to switch 16 where financial approval transactions are required.

As previously recited, the present invention facilitates multiple retailers to automate the process of matching items presented at POS 26 purchase with the buyer selected payment mechanism to determine if the items presented are permitted to be purchased by the presented payment mechanism. More particularly, the present invention provides for the matching of items to multiple item lists for sponsor associated payment/settlement programs.

Figure 2:
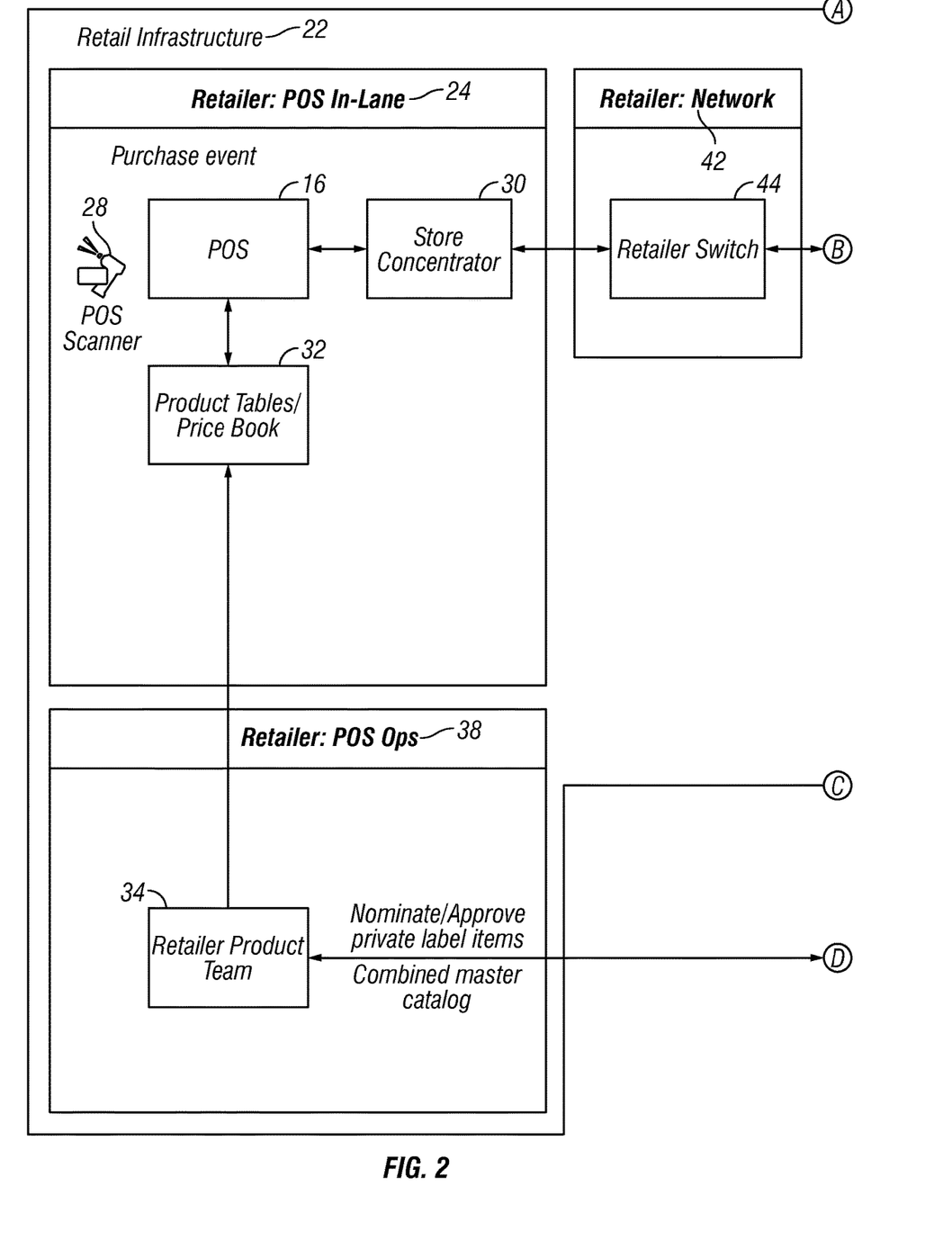
FIG. 2 is an overall system architecture of one embodiment of the present invention inside a retailer network infrastructure.

In the FIG. 2 embodiment, the adjudication processor 10 is included in the retail infrastructure 22. The overall system architecture in the FIG. 2 embodiment includes switch 58 to communicate with retailer processes that are behind the retailer firewall.

The adjudication process utilizes components in the adjudication processor 10. In combination, the switch 16, market basket analysis server 12, catalog management server 36, and the process control server 14 provide adjudication. In one embodiment, the adjudication process also can authorize the financial transaction.

Financial transactions that are triggered by a retailer in-lane purchase activity are typically communicated in the form of ISO 8583 from the retailer switch 44 to the switch 16. The switch 16 decomposes the ISO 8583 message into messages suitable for processing by subsequent processing components, such as the market basket analysis server 12.

In one embodiment, the switch 16 communicates the market basket content data and transaction identification information to the market basket analysis server 12, in the data form that has been parsed and formatted by the switch 16.

The market basket analysis server 12 compares the market basket contents to the product catalog(s) 18. Product catalog (s)18 have been previously loaded to market basket analysis server 12 from catalog management server 36. Product catalogs 18 contain an items list of approved products, identified by UPC and short description. Market basket line item content data is processed iteratively by the market basket server 12.

With the present invention, adjudication to a plurality of catalogs 18 can be processed. With the present invention, a catalog 18 is directly related to an account purse. This purse can be associated to a restricted spend based upon the catalog 18 that is used to adjudicate an item list. For example, a financial transaction financial transaction card may support spending against a food items catalog and also an over-the-counter drug item catalog. One or more spending purses, each with a specific spending balance from a specific Issuer may be identified to a single financial transaction financial transaction card.

With the present invention, the retailer 24 collects the market basket and upon a swipe or scan of a buyer's financial transaction financial transaction card, packages up the market basket sends it to the adjudication processor 10 with either, (i) the retailer processing the purchase request, or (ii) the adjudication processor processing the purchase request. Incoming and outgoing communications between the retailer 24 and the adjudication processor 10 can via an ISO 8583 message format, an XML web services format, and the like, all as real time interchanges. As a non-limiting example, entering can be done by at least one of, swiping the financial transaction financial transaction card through a slot of a financial transaction card reader coupled to the mobile device, through a slot of the mobile device, scanning, through wireless communication, touch of the financial transaction financial transaction card to the mobile device, by typing in information at the mobile device, photos, selecting a financial transaction financial transaction card from an application on a mobile device and from an on-line entity.

As illustrated in FIGS. 1 and 2, the retailer communicates with the retailer switch 44 which pushes transaction data to the adjudication processor 50. The switch 16 receives the transaction and processes it to conclusion. The switch 16 is the gateway for all types of transactions. A transaction may be one of many types. In one embodiment of the invention a transaction may be an adjudication request, an authorization request, or a POS result transaction. The switch 16 determines the nature of the transaction request 56 and formats data and routes the request through subsequent processes as determined by the type of request.

Figure 3:
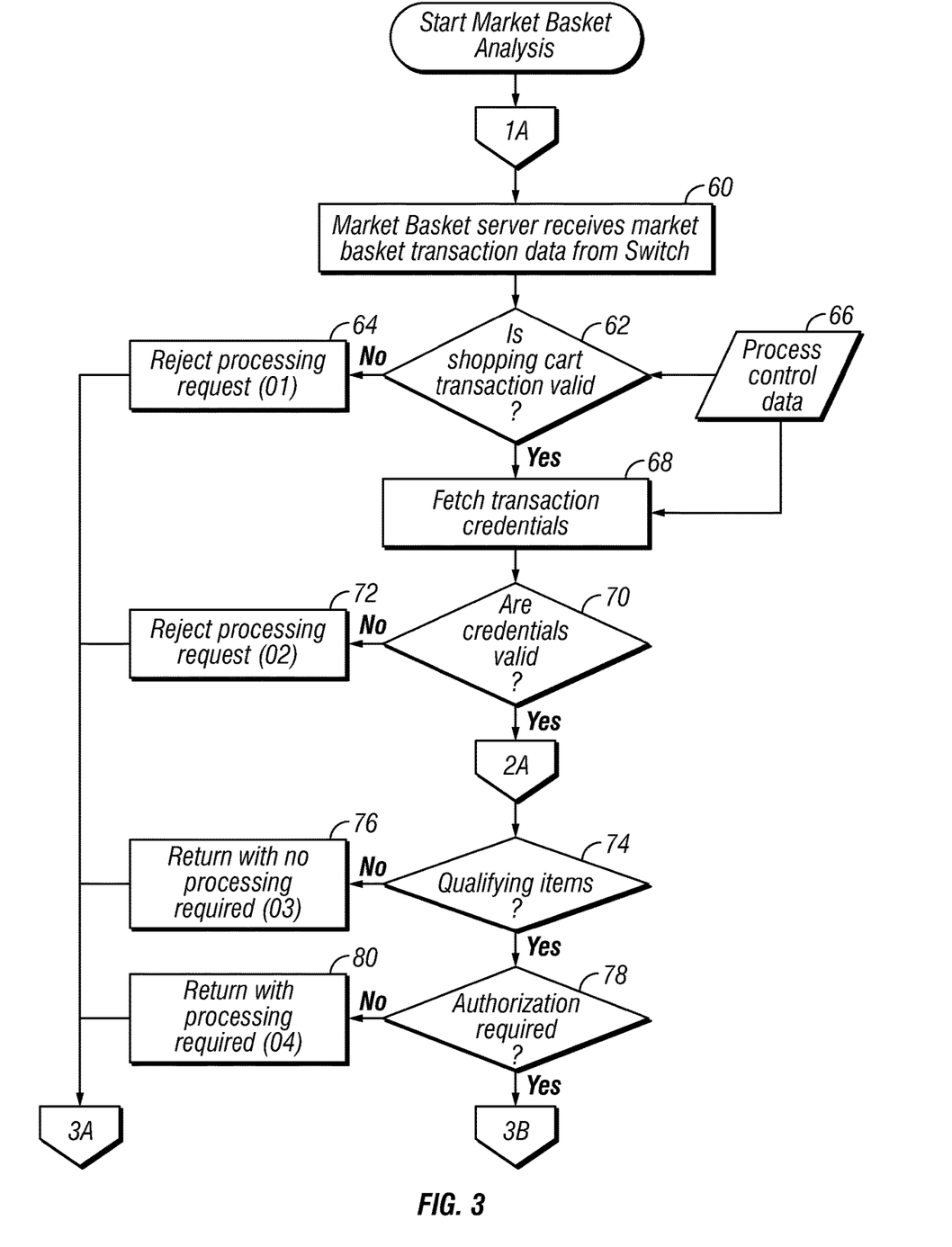
FIG. 3 is a flow chart illustrating operation of a market basket analysis server used in one embodiment of the present invention.

FIG. 3 is a flow chart illustrating operation of the market basket server 12 with steps 60-80. The market basket analysis server receives market basket transaction data from the switch 16 and determines if the market basket transaction is valid. If it isn't, then the processing request is rejected. If it is valid, then the market basket server 12 retrieves transaction credentials from process control data. If the credentials are not valid then the processing request is rejected. When the credentials are valid, a determination is made to see if there are qualifying items from the market basket. If not then the there is a return with no processing required. If yes, authorization is required and then returned with processing required.

The adjudication transaction contains transaction identification and market basket information as formatted and forwarded to the market basket server process. The authorization transaction contains transaction identification and requests for financial authorization against a specific financial payment account (purse). The result transaction contains transaction identification information, processed market basket adjudication transaction (market basket items flagged to a specific purse and catalog), and financial authorization information.

The market basket server 12 receives an adjudication transaction from the switch 16. The market basket server 12 processes the entire financial transaction financial transaction card to the extent possible and returns the transaction result to the switch for further processing as required. The switch 16 receives the adjudication transaction and determines if further processing is required. The adjudication transaction may require that the switch 16 obtain financial transaction authorization from one or more issuers. The switch 16 formats the transaction information 60 for routing and processing by the issuer.

The switch 16 waits to complete a transaction to the retailer 24 until authorization request(s) are processed and returned by the issuer(s). Authorization information is formatted and returned to the retailer 24 and the transaction is added to a permanent data log of all transactions passing through the switch 16. The switch 16 formats POS result transaction and returns to the retailer 24 and the transaction is added to a permanent data log of all transactions passing through the switch 16.

Figure 4:
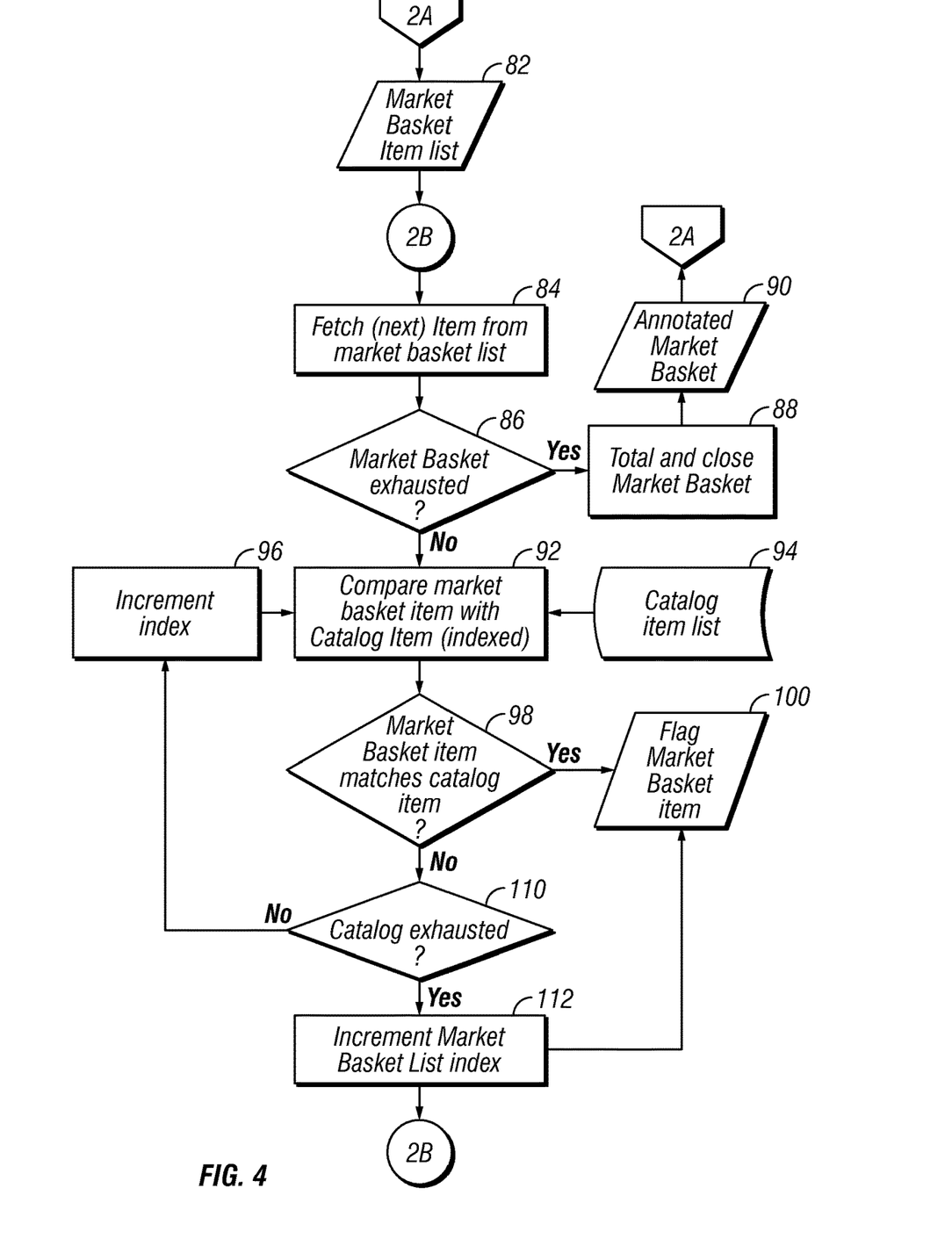
FIG. 4 is a flow chart illustrating market basket adjudication in one embodiment of the present invention.

Referring to the market basket adjudication flow chart of FIG. 4 with steps 82 through 112, the market basket item list is received using the market basket analysis server 12 and the switch 16. When the market basket is exhausted a total is made of the items, the market basket is closed, and an annotated market basket created. If it is not exhausted then items from the market basket are compared with indexed catalog items. When there isn't a match with catalog items the catalog 18 is exhausted and an index incremented. Then the catalog 18 is not exhausted the market basket list index is incremented and the item is flagged.

Figure 5:
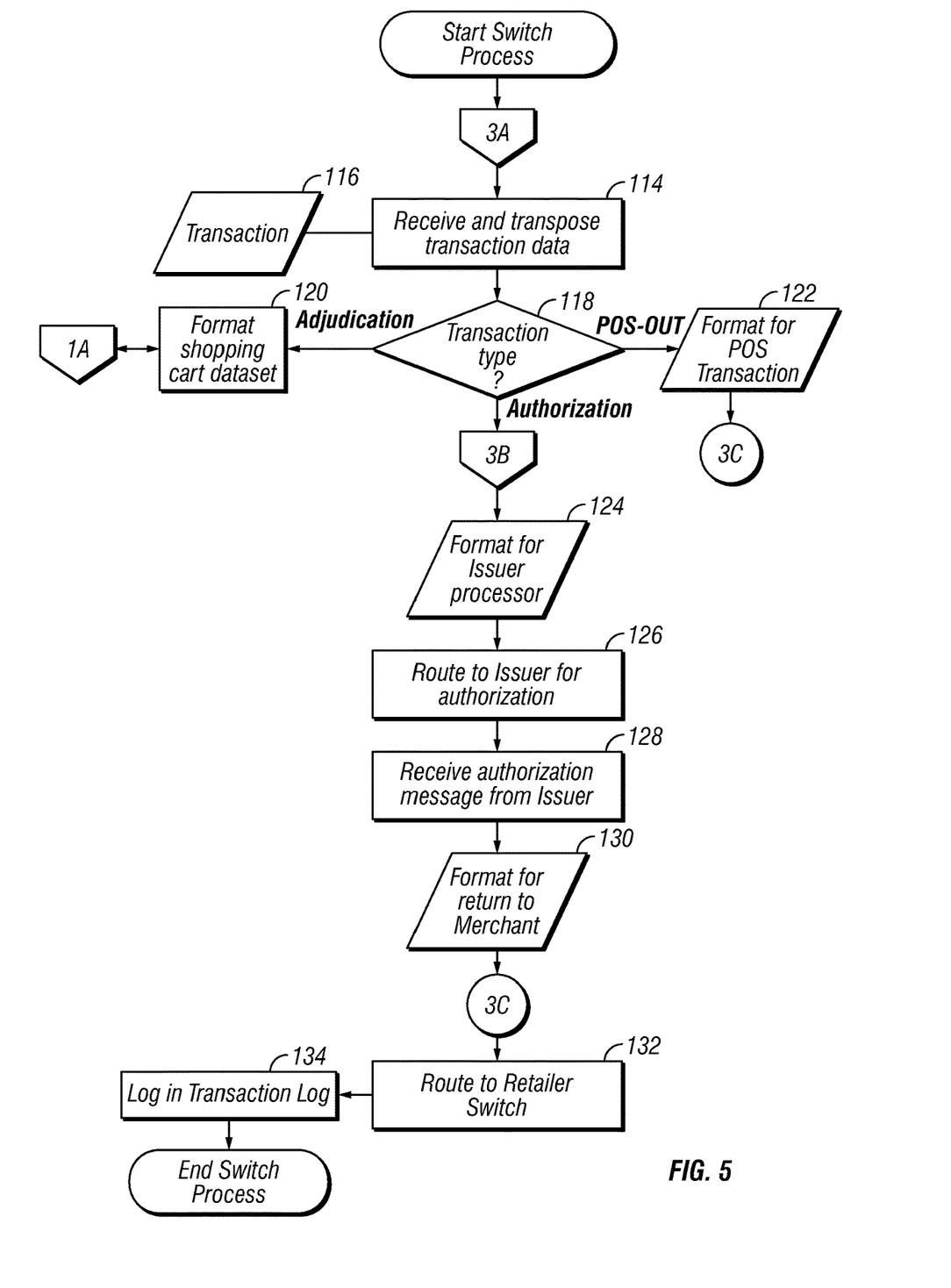
FIG. 5 is a flow chart illustrating the operation of a switch of an adjudication processor in one embodiment of the present invention.

The operation of the switch 16 is illustrated in FIG. 5 in steps 114 through 134. The switch 16 receives and transposes transaction data received from a transaction. A determination is made by the switch 16 as to the type of transaction. When the transaction is adjudication, the market basket is formatted. For a POS-OUT transaction, it is formatted for POS. The switch 16 then performs authorization, formats the transaction for the financial processor 46 and then routes 508 to the issuer for authorization. An authorization message 509 is received from the financial processor 46. The switch 16 formats this and returns it to the retailer 24 via the retailer switch 44. The transaction is then logged in a transaction log.

There are multiple authorizations for multiple purses. The switch 16 is configured to couple to multiple financial processors 40 when there are multiple authorizations. The switch 16 can couple to multiple financial processing systems, to process restricted spending against multiple purses tied to multiple issuer processors. Based upon rules provided by the process control server 14, the switch bifurcates the financial transactions to multiple financial financial transaction card issuers and receives authorization from multiple financial processors.

With the present invention the market basket analysis server 12 isolates a buyer's financial account information from the reliance for regulatory compliance of HIPAA and PCI-DSS.

The retailer 24 is isolated from the details of multiple purses, multiple financial transaction financial transaction card issuers member demographics and the like. The PAN of a transaction ties to an account structure that defines the applicable process control rules. Process control rules are provided to the switch 16 from the process control server 14, to establish the path of the financial authorizations. A financial transaction financial transaction card number 48 and associated catalogs 18 with that financial transaction financial transaction card are provided in order for the market basket analysis server 12 to use the catalogs with a purse.

The adjudication processor 10 does not send the retailer member demographics. A financial transaction financial transaction card number 48 and associated catalogs 18 with that financial transaction financial transaction card are provided in order for the market basket analysis server 12 to use the catalogs related to the PAN, financial transaction financial transaction card issuers, and purses.

With the present invention the following steps are taken. A collection of item data is received, e.g., the market basket. Each item in the market basket has a universal product code ("UPC") to uniquely identify the item and has a quantity, net price and added tax as determined by the retailer price list.

Each item in a market basket is evaluated and compared by the UPC to items approved for the specific purse as related to the product/plan product catalog 18. Each item in the market basket is marked as eligible or ineligible to a specific product/plan. Eligible items are grouped according to a product/plan and a calculation is made of a total cost of all items, less appropriate discounts and allowances, for each group. Items, group totals, and market basket identification information is formatted into XML data structures, ISO8583, NCPDP 5.1 or NCPDP d.0, for further processing by the retailer 24, benefit processor 52 and the like.

Adjudication can be hosted at a retailer 24 and be internal to the retailer, or adjudication can be hosted external to the retailer and have several retailers connecting to it.

XML data structure is pushed to the switch 16. The switch 16 is utilized to translate data in the retailer specified format for systems hosted within the retailer network and into ISO8583, XML, NCPDP 5.1 or NCPDP d.0 formats for processing by issuer processor 50 or claims processor 54. An XML-based financial authorization request or ISO8583 based financial authorization request is initiated where the financial processor is not integral to the internal retailer network, and where the retailer requires that transactions be initiated by the present invention. In this instance, the system and method of the present invention process control server 14 determines the content of the authorization request against group totals and the switch 16 builds and transmits XML-based authorization requests to the financial processor 46. The switch 14 formats XML-based authorization requests in formats required by the corresponding issuer processor.

Items selected by the buyer and placed in the market basket are presented for purchase to the check out process of the participating retailer 24. This process may be a physical lane within a retail store, a collection of market basket items selected from a catalog and identified by the buyer at the time of check out, or the presentation of a script at a retail store, on-line or telephone based pharmacy counter, among other processes.

The process of using the retailer physical checkout lanes or the retailer physical pharmacy counter requires that market basket items be scanned or hand entered into the retailers store POS 26. The process of using catalog 18, on-line or telephone shopping requires that items be selected and identified by the shopping method and entered as items in the market basket.

Regardless of the method of shopping, all market basket item data, including price, quantity, taxes, point-of-purchase driven discounts are packaged into a single transaction and formatted according to the stores point-of-sale system message specifications. The single transaction must also include retailer identification information and buyer identification information, which at a minimum can include:
 1. Retailer ID
 2. Store ID
 3. Terminal ID
 4. PAN—Primary Account Number
 5. Timestamp
 6. STAN—System Trace Audit Number
 7. Line item detail <per unique market basket item>
  a. UPC
  b. Net price
  c. Tax
  d. Quantity
  e. Brief item description This transaction comes from the POS 26 to the store concentrator 30 to retailer switch 44 and then to the switch 16. The transaction data can include item data and customer identifier (financial transaction financial transaction card number) data, and the like. Communication is via the retailers 24, store concentrator 30 and to the retailer switch 44. All of the retailers 24 are connected to the network, and data goes from the retailer switch 44 to the retainers 24, and then to another switch inside the retailer. The switch 16 utilizes the retailer switch 44 or to an internal retailer switch with communications to the retailer 24 being in a variety of methods, including but not limited to, ISO 8583 or XML data structures.

Transaction data is received from the originating retailer 24. The market basket transaction is directed from the market basket server 12 to the switch 16. The switch 16 formats the data into an XML data structure, from whatever retailer structure that was received, and transmits the translated XML structure to the market basket analysis server 12.

The market basket analysis server 12 utilizes the PAN to determine the catalogs 18 and purses for the buyer account. The buyer's personal information is not retrieved at any point in during adjudication or financial transaction processing. The buyer PAN relates one or more specific product catalogs to the market basket transaction.

If the buyer identifier, e.g., the account number of a financial transaction financial transaction card (PAN) is not recognized by the switch 16, an error occurs and there is a rejection. If the PAN there is an error, the switch 16 returns a message to the originating retailer 24 that the transaction is declined.

The switch 16 matches the item data received in the market basket transaction, one item at a time. The switch 16 appends two indicators to each line item of the market basket. A flag is produced that communicates if the item is eligible or not eligible, and an indicator of the group (catalog) 18 is also determined to which the item belongs.

Upon completion of processing, each item in the market basket and totals by each group are used to package the market basket transaction and returned to the retailer 24 for processing. In another embodiment, the processed market basket transaction is returned to the switch 16.

Upon receipt of the processed market basket transaction the market basket analysis server 12 matches the buyer identifier to the financial transaction financial transaction card issuer associated with the buyer identifier.

The switch 16 creates an XML-based payment authorization request message that includes financial processor 46 identification and retailer transaction identification information. This payment authorization is then sent to the financial processor 46. In various embodiments, ISO 8583, XML and NCPDPd.0 data structures are used for the authorization request messages between the switch 16 and the financial processor 46.

In various embodiments, the switch 16, (i) receives an authorization message back from the financial processor 46 or claims processor 54; (ii) creates a data log of authorized transactions based upon transaction identification number and (iii) creates an authorization message in the proper format to forward the message to the retailer 24.

In another embodiment of the present invention, the catalog management processor 40 creates a catalog 18 of UPC's for each of a participating retailer 24. Each catalog 18 includes first and second sets of UPC data. The first set is for national brand products and the second set for retailer 24 private label products.

The system and methods of the present invention enable inComm retailers 24 to accept a financial transaction card based payment method at the point of sale for products, including but not limited to medicine and medical supplies, covered by a sponsor, including but not limited to Medicare and/or Medicaid. The present invention provides systems and methods which enable a replacement for reimbursement methods which have traditionally included manual claims or offline systems which do not interact with a retailer's 24 POS 18.

In some cases, the financial transaction card acceptance/redemption mechanism leverages existing POS-to-inComm messaging interface for transaction processing.

In another embodiment of the present invention, a Pseudo-prescription is created that contains an NDC for each over-the-counter item being purchased prior to determining if the claims processor 54 supports real-time authorization. If it is determined that the claims processor 54 can support a real-time authorization request, then an NCPCP formatted claim authorization request message is sent to the claims processor 54. The market basket analysis server 12 contacts the benefit processor 52 via the switch 16 in real time to originate and receive a claim authorization.

The retailer:POS 24 submits a market basket through the retailer switch 44 to adjudication processor switch 16. The switch 16, based upon rules provided by the process control server 14, formats an NCPDP claim transaction for the items in the market basket. The switch 16 waits to complete a transaction to the retailer 24 until NCPDP Claim transaction (s) are processed. If the switch 16 system determines that the claims processor 54 can not support a real-time authorization request, then the switch 16 compares the previously retrieved financial transaction card available balance, from financial processor 46, to the amount requested in the transaction data received from the originating retailer. If the balance is less than the amount requested, then the switch 16 sends a decline to the originating retailer 24. If switch 16 determines if the balance is equal to or greater than the amount requested, then switch 16 submits the NCPDP Claim transaction to the claim processor 54 for approval. Upon receipt, the claims processor 54 formats a NCPDP Claim approval message to the switch 16, switch 16 re-attaches the item data to the authorization message and submits it back to the originating retailer 24. A data log of the transaction is created and submitted to the data store.

Other embodiments of the invention will be apparent to those skilled in the art from consideration of the specification and practice of the invention disclosed herein. It is intended that the specification and examples be considered as exemplary only, with a true scope and spirit of the invention being indicated by the appended claims.

What is claimed is:

1. A method for creating a pseudo-prescription for over the counter items that do not require prescriptions, and using the pseudo-prescription in a purchase transaction, the method transacted amongst an adjudication processor in communication with a benefits processor, a financial processor, and a retail infrastructure, the adjudication processor including a market basket analysis server, a switch, one or more product catalogs, and buyer account data associated with a buyer, the method comprising:
   receiving an identifier of a buyer account associated with the buyer, the identifier comprising a primary account number (PAN);
   determine based on the PAN and in communication with the catalog management server a specific plan, with eligible items set forth in one or more applicable product catalogs;
   providing the retailer infrastructure that includes a point of sale server coupled to a store concentrator;
   providing the adjudication processor and benefits processor with a process control server;
   pursuant to the specific plan, creating a pseudo-prescription by the retailer infrastructure for the over-the-counter non-prescription item that does not require a prescription, the pseudo prescription for each over-the-counter item being purchased and formatted as a National Council for Prescription Drug Programs (NCPDP) claim transaction for the items in the market basket, the pseudo-prescription being used in a purchase transaction of the non-prescription item to associate each over-the-counter item with the buyer's plan and benefit coverage of such plan;
   and determining that the benefits processor does not support real-time authorization requests and comparing by the switch the previously retrieved financial transaction card available balance to an amount requested in transaction data from the retailer, and:
   determining that the balance is sufficient to cover the authorization request and submitting the transaction to the benefits processor for processing;
   upon receipt at the benefits processor, formatting a NCPDP Claim approval message to the adjudication processor switch, which re-attaches item data to the authorization message and submits it back to the point of sale server;
   wherein the retail infrastructure is isolated from details of multiple purses and the buyer's personal information.

2. The method of claim 1, wherein the adjudication processor switch waits to complete a transaction to a retailer until the NCPDP Claim transaction(s) are processed.

3. The method of claim 1, wherein if the balance is less than an amount requested, the adjudication processor switch sends a decline to the originating retailer.

4. The method of claim 3, wherein when the adjudication processor switch determines if the balance is equal to or greater than the amount requested, then the adjudication processor switch submits the NCPDP Claim transaction to the claim processor for approval.

* * * * *